(12) United States Patent
Goldstein et al.

(10) Patent No.: US 6,706,026 B1
(45) Date of Patent: Mar. 16, 2004

(54) INSTILLATION UTERINE CATHETER

(75) Inventors: Steven R. Goldstein, New York, NY (US); Rodney W. Bosley, Jr., Bloomington, IN (US)

(73) Assignee: Cook Urological Incorporated, Spencer, IN (US)

( * ) Notice: Subject to any disclaimer, the term of this patent is extended or adjusted under 35 U.S.C. 154(b) by 1194 days.

(21) Appl. No.: 08/689,400

(22) Filed: Aug. 9, 1996

(51) Int. Cl.[7] .............................................. A61M 31/00
(52) U.S. Cl. ....................................... 604/278; 604/279
(58) Field of Search .................................. 604/164, 275, 604/279, 55, 278, 264, 280; 606/119, 193

(56) References Cited

U.S. PATENT DOCUMENTS

| | | |
|---|---|---|
| 3,626,928 A | 12/1971 | Barringer et al. |
| 4,071,027 A | 1/1978 | Meador |
| 4,089,337 A | 5/1978 | Kronner |
| 4,119,098 A | 10/1978 | Bolduc et al. |
| 4,430,076 A | 2/1984 | Harris |
| 4,441,509 A | 4/1984 | Kotsifas et al. |
| 4,601,698 A | 7/1986 | Moulding, Jr. |
| 4,997,419 A | 3/1991 | Lakatos et al. |
| 5,100,382 A | 3/1992 | Valtchev |
| 5,147,315 A | 9/1992 | Weber |
| 5,195,964 A | 3/1993 | Kletzky et al. |
| 5,217,466 A | 6/1993 | Hasson |
| 5,259,836 A | 11/1993 | Thurmond et al. |
| 5,338,297 A | 8/1994 | Kocur et al. |
| 5,364,375 A | 11/1994 | Swor |
| 5,421,346 A | 6/1995 | Sanyal |
| 5,431,662 A | 7/1995 | Nicholas |

OTHER PUBLICATIONS

Steven R. Goldstein, MD; "Unusual Ultrasonographic Appearance of the Uterusin Patients Receiving Tamoxifen"; vol. 170, No. 2, Feb. 1994; Clinical Section; pp. 447–451.
Anna K. Parson, MD, and Jorge J. Lense, MD;"Sonohysterography for Endometrial Abnormalities: Preliminary Results"; Journal of Clinical Ultrasound vol. 21, No. 2, Feb. 1993; pp. 87–95.

Primary Examiner—Brian L. Casler
(74) Attorney, Agent, or Firm—Brinks Hofer Gilson & Lione

(57) ABSTRACT

A device is provided for instilling a fluid into the cavity of the uterus which avoids various disadvantages inherent in prior art devices, e.g., patient discomfort, an adjustable seal to accommodate varying dimensions of the uterus of the patient, a non-invasive, non-surgical procedure that could be performed in a relatively short period of time with little risk to the patient. The device provides a simple design to accomplish the ends described above and avoiding more complex designs including more complex procedures inherent in prior art devices. Moreover, the device and procedure may provide an even more definitive and reliable diagnostic means for the detection of abnormalities, polyps and tumors and to measure and monitor endometrial thickness within the uterus.

23 Claims, 2 Drawing Sheets

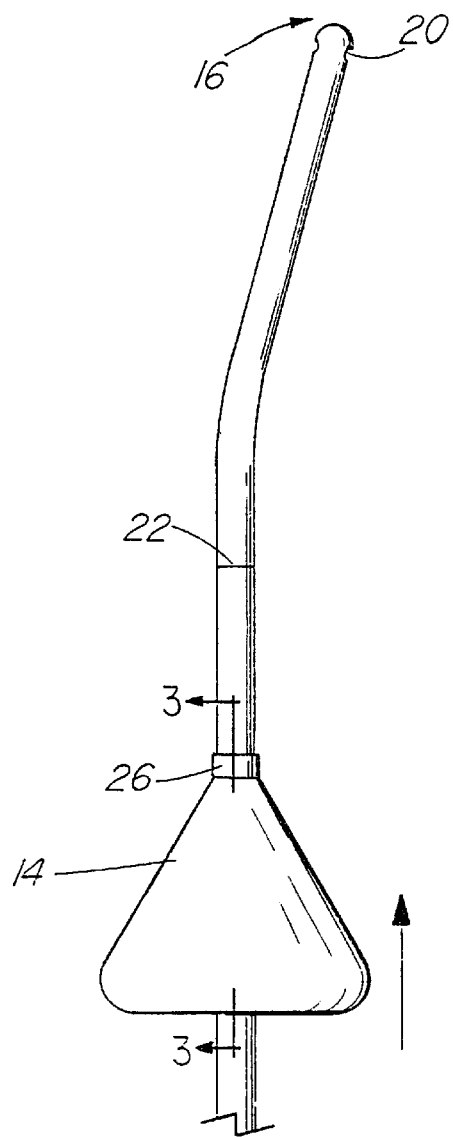
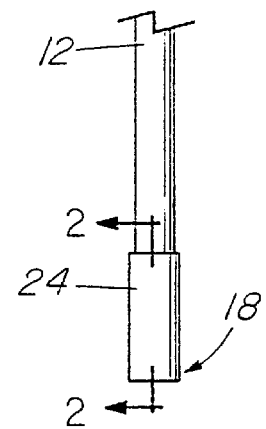
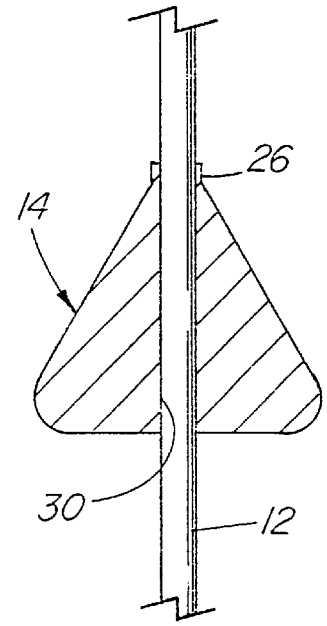
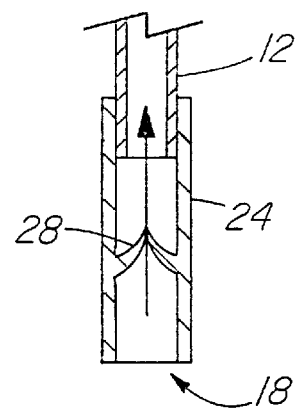
FIG. 1
FIG. 2
FIG. 3

INSTILLATION UTERINE CATHETER

FIELD OF THE INVENTION

This invention relates to a device for expediting the non-invasive infusion of a fluid into the uterine cavity. More specifically, the device provides a single step procedure for infusing fluid through a single catheter and sealing the uterus with an adjustable seal in order to perform therapeutic and/or diagnostic procedures.

BACKGROUND OF THE INVENTION

A number of conditions require the non-invasive entry into the uterine cavity, for both therapeutic and diagnostic purposes. Such access is provided through the canal of the uterocervix, transvaginally for diagnostic purposes. Contrast media and/or image enhancing media may be injected into the cervical canal and radiography, sonohysterography may be carried out, to, e.g. establish the outline of the uterine cavity and/or patency of the Fallopian tubes, to diagnose or determine the development of polyps and/or submucous myomas.

Non-invasive access to the Fallopian tubes is also utilized for the purposes of artificial insemination as well as diagnostic reasons. Typically, this procedure, which has been shown to be at least twice as effective as in vitro fertilization, involves harvesting the eggs and injecting a mixture of sperm and egg into the Fallopian tubes. While this procedure can be carried out under hysteroscopic, radiographic or ultrasonographic control, the common denominator of all of these procedures is access through the cervical canal and insertion of multiple catheters into the tubes. Another possible use of selective tubal catheterization is to inject compositions for the purpose of reversible sterilization.

A number of devices have been designed for the purposes discussed above, however, most of them involve multiple catheters and thus generally requiring multiple procedural steps as well as utilizing sealing devices, e.g., balloons, which may increase the discomfort to the patient as well as requiring longer time for carrying out the procedure.

Other alternative diagnostic procedures for such conditions as polyps or myomas are generally surgical procedures, such as hysteroscopy; but involve a greater risk to the patient, are not always definitive, as well as requiring much longer time to carry out the procedure for a less definitive diagnosis, and a greater expense.

Thus, a device is needed for infusing or instilling a fluid, e.g., an image enhancing fluid such as saline, for instillation sonohysterography or other similar diagnostic and/or therapeutic procedures. Also, the device requires a seal for the cervical opening that may be adjustable as well as avoiding the pain and cramping that may arise by the use of an inflation membrane, e.g., a balloon.

SUMMARY OF THE INVENTION

In accordance with the present invention, a device for instilling, i.e., infusing, a fluid into the uterine cavity for various diagnostic and/or therapeutic purposes is provided.

Further in accordance with the present invention, a method is provided for infusing a fluid into the uterus for diagnostic and/or therapeutic procedures.

Still further in accordance with the present invention, a device is provided for a non-invasive infusion of a fluid in the uterine cavity wherein the device comprises an elongated tubular body having proximal and distal ends;

a slidable cervical seal located on the tubular body and slidable along the entire length of the tubular body wherein the seal engages the opening of the cervix and at least partially seals the cervix opening from the discharge of fluid contained within the uterus;

an opening in the distal end of the tubular body to allow the discharge of fluid and the proximal end adapted to deliver fluid to the uterus thru the opening in the distal end.

Still further in accordance with the present invention, a device is provided for the non-invasive infusion of fluid into the uterus wherein the device comprises an elongated tubular body having a slidable cervical seal positioned on the tubular body and the cervical seal has a conical shape having a neck at the distal end of the seal for easily engaging the cervical opening.

Still further in accordance with the present invention, a specific method is provided for detecting polyps or tumors within the uterus and for determining or monitoring endometrial thickness by using the device of the present invention for saline instillation sonohysterography.

Still further in accordance with the present invention, a method and device is provided for instilling fluid within the uterus while avoiding discomfort and cramping to the patient by providing a device wherein the cervical seal of the device will allow liquid to leak around the seal in the event the fluid pressure within the uterus becomes too high.

To the accomplishment of the foregoing and related ends, the invention, then, comprises the features herein after fully described and particularly pointed out in the claims. The following description and the annexed drawings setforth, detail certain illustrative embodiments of the invention. These embodiments are indicative, however, of but a few of the various ways in which the principles of the invention mentioned may be employed. Other objects, advantages and novel features of the invention will become apparent from the following detailed description of the invention when considered in conjunction with the drawings.

BRIEF DESCRIPTION OF THE DRAWINGS

The invention will be further described in connection with the attached drawing figures showing preferred embodiments of the invention including specific parts and arrangements of parts. It is intended that the drawings included as a part of this specification be illustrative of the preferred embodiment of the invention and should in no way be considered as a limitation on the scope of the invention.

FIG. 1 is a perspective view of one embodiment of the device according to the present invention.

FIG. 2 is a cross section along line 2—2 of the proximal end of the device according to the present invention.

FIG. 3 is a cross section along line 3—3 of the cervical seal and elongated tubular body in accordance with the present invention.

DETAILED DESCRIPTION OF THE PREFERRED EMBODIMENTS

Figure 4:
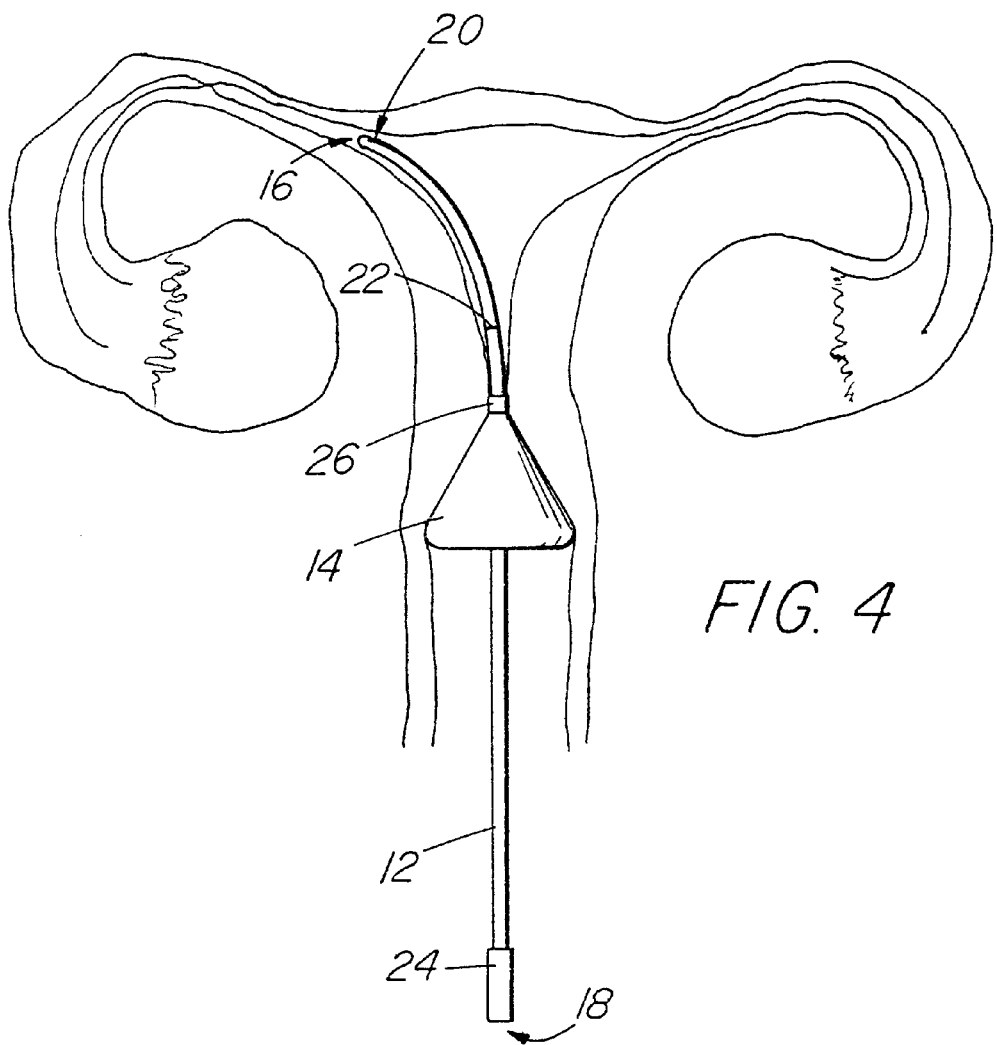
FIG. 4 is a schematic, front view of the intrauterine cavity and a device according to a preferred embodiment of this invention.

The device according to the present invention provides a very simple design while providing an effective, safe non-invasive procedure for instilling fluid into the uterine cavity for various diagnostic and/or therapeutic purposes. Because sonohysterography has become a valuable diagnostic tool for detecting polyps and tumors, e.g., submucous myomas, as well as monitoring patients receiving Tamoxifen, the device of the present invention is particularly useful for instilling saline into the uterine cavity and sealing the uterine cavity after the infusion of saline in order to enhance the ultrasound image.

A more detailed description of the present invention will now be given with reference to FIGS. 1–4. FIG. 1 is a perspective view of a preferred embodiment of the device according to the present invention. The device according to the present invention first comprises a catheter 12. The catheter 12 is an elongated tubular body derived from a flexible material, most preferably a clear flexible material, e.g., polypropylene, polyethylene and the like. Located on and engaging the surface of the catheter body is cervical seal 14 that may slide along the entire length of tubular body 12. In an alternative embodiment the cervical seal 14 may be fixed on the catheter body at approximately 7 cm from the tip of the distal end 16. The catheter 12 further comprises proximal end 18 which contains neck 24 adapted to receive a fluid delivery means for instilling a fluid into the catheter to discharge from distal end 16 through opening 20 and into the uterine cavity. The proximal end 18 further comprises a one-way valve to avoid producing air bubbles in the fluid to be infused into the uterus. It is pointed out that distal end 16 may be open or closed (as shown) having opening or port 20 just below the tip of distal end 16. Alternatively, FIG. 5 shows distal end 16 having open tip 20 as an optional embodiment according to the present invention. The catheter may preferably contain a mark 22 at approximately 7 cm from the distal end 16 which is typically the longitudinal length of the uterus. The cervical seal 14 also comprises neck 26 which assists and makes it easier to engage the cervix opening and will typically engage the cervix opening at the mark 22.

Referring now to FIG. 2, the proximal end 18 is shown as a cross section along lines 2—2 of FIG. 1. The elongated tubular body 12 is shown engaging and attached to the barrel neck 24 requires and in a preferred embodiment comprises one way valve 28. The barrel neck 24 preferably is produced from a stiffer material than the flexible material making up the tubular body of the catheter 12. The barrel neck 24 requires to be adapted to merely receive a fluid delivery means, e.g., a syringe or attachment to a cylinder fluid delivery device and the like.

In FIG. 3, a section of the cervical seal 14 and catheter 12 along lines 3—3 of FIG. 1 is shown. The cervical seal 14 has preferably a conical shape with neck 26 for engaging the cervix opening. Also, cervical seal 14 engages the wall of catheter 12 at interface 30 and while cervical seal 14 may slide on the external wall of catheter 12, it requires a sufficiently secure engagement with the wall of the catheter in order to prevent fluid leakage along interface 30. Alternatively, the cervical seal 14 may be fixed at 7 cm or at mark 22 on the catheter wall. Thus the catheter 12 and cervical seal 14 may be produced, e.g., by molding the device as a single unit.

The cervical seal is preferably produced from a biocompatible elastomeric material. Most preferably it is prepared from a silicone rubber, e.g., SILASTIC® Q7-4850 available through Dow Corning.

Figure 5:
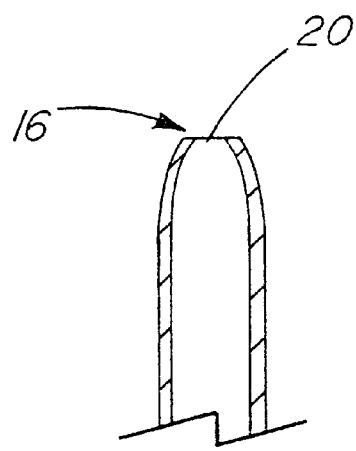
FIG. 5 is a sectional view of one embodiment of the distal tip for the device according to a preferred embodiment of the invention.

FIG. 4 illustrates an instillation uterine catheter according to the present invention seated in the patient's cervix showing cervical seal 14 with neck 26 engaging the cervix opening. The tubular catheter 12 is positioned transvaginally into the uterus where a fluid may be delivered to the uterus through proximal end 18 and is discharged into the uterus at distal end 16 through opening 20.

Cervical seal 14 seals the liquid in the uterus and yet does not provide such a tight seal that if the pressure of the fluid within the uterus increases to the point where it may create discomfort to the patient, the seal will allow leakage around the neck 26 in order to relieve the pressure increase by the fluid contained within the uterus.

In a preferred embodiment according to the present invention, the catheter 12 will have an outer diameter ranging from about 0.039 inch to about 0.158 inch. In a most preferred embodiment the outer diameter is about 0.066 inch to about 0.07 inch. Also, the length of the catheter 12 may range from about 10 cm to about 35 cm and most preferably the catheter 12 has a length of 23 cm. The port 20 may form the tip of distal end 16 as illustrated in FIG. 5 or may be located up to about 4 cm from the tip of the catheter, i.e., distal end 16.

With respect to the dimensions of the cervical seal 14, the outer diameter of the cone may range from about 0.500 inch to about 0.750 inch and most preferably an outer diameter of about 0.600 inch. The longitudinal length of the cone may range from about 0.750 inch to about 1.75 inches and most preferably the length is about 1.1 inches. The angle of where the neck 26 of the cone 14 meets the surface of cone 14 may range from about 6.0° to about 27° and is most preferably about 16.5°.

While the device according to the present invention may be utilized to deliver a therapeutic agent into the uterus, in its most preferable application, it is utilized for delivery of an image enhancement media, e.g., saline, for enhancing the image of an ultrasound image to detect abnormalities, polyps, tumors, determining and/or monitoring the thickness of the endometrial wall, and the like within the uterus.

As is evident, the device according to the present invention provides a very effective yet simple design for delivering fluids into the uterine cavity and avoiding the more complex designs of the prior art. Many of the prior art devices require multiple catheters, collars and the like. Moreover, the cervical seal 14 provides the advantage that the seal may be adjusted to accommodate patients having different and varying uterine dimensions as opposed to those devices wherein the seal is affixed to the particular instrument of device. Also, the seal is designed such that it will provide leakage if the build-up of pressure is too high so as to potentially cause discomfort to the patient. This design provides a particular advantage over inflatable seal designs such as balloons and the like as that disclosed in U.S. Pat. No. 5,100,382.

The foregoing description and drawings are provided for illustrative purposes only and are not intended to limit the scope of the invention described herein or with regard to the details of its construction and manner of operation. It will be evident to one skilled in the art that modifications and variations may be made without departing from the spirit and scope of the invention. Changes in form and in the proportion of parts, as well as the substitution of equivalence, are contemplated as circumstances may suggest and render expedience; and although the specific terms have been employed, they are intended in a generic and descriptive sense only and not for the purpose of limitation, the scope of the invention is setforth in the following claims.

What is claimed is:

1. A device for expediting the non-invasive infusion of a fluid into the uterine cavity comprising:
   an elongated tubular body having proximal and distal ends;
   a slidable cervical seal located on the tubular body and slidable along the entire length of the tubular body wherein said is capable of engaging seal engages the opening of the cervix and at least partially seals said cervical opening from the discharge of fluid contained within the uterus; and
   an opening in the distal end of said tubular body to allow the discharge of fluid;
   wherein the proximal end of the elongated tubular body is adapted to deliver fluid into the uterus, and wherein said proximal end further comprises a one-way valve to avoid producing air bubbles in the fluid to be infused in the uterus.

2. The device according to claim 1 wherein said cervical seal is comprised of an elastomeric material and further seals the interface of said cervical seal and the elongated tubular body from leaking fluid.

3. The device according to claim 2 wherein said elastomeric material is a silicon rubber of biomedical grade.

4. The device according to claim 1 wherein said distal end of said elongated tubular body includes a tip which is closed and is rounded.

5. The device according to claim 1 wherein said distal end of said elongated tubular body includes a tip which is open.

6. The device according to claim 1 wherein said fluid is an image enhancing media for conducting various diagnostic procedures in the uterus and fallopian tubes.

7. The device according to claim 1 wherein said cervical seal has a conical surface and a neck at the distal end of said seal engaging the elongated tubular body to avoid any leakage of liquid at the interface of the elongated tubular body and cervical seal while providing a structure to more easily engage the cervical opening.

8. The device according to claim 1 wherein a mark is provided at about 7 cm from the distal end to assist in positioning the elongated tubular body in the uterus.

9. The device according to claim 1 wherein said elongated tubular body is comprised of a clear, flexible material.

10. The device according to claim 1 wherein said cervical seal is fixed about 7 cm from the distal end on said elongated tubular body.

11. A device for expediting the non-invasive infusion of a fluid into the uterine cavity comprising:
    an elongated tubular body having proximal and distal ends;
    a slidable cervical seal located on the tubular body and slidable along the entire length of the tubular body wherein said seal engages the opening of the cervix and at least partially seals said cervical opening from the discharge of fluid contained within the uterus; and
    an opening in the distal end of said tubular body to allow the discharge of fluid;
    wherein the proximal end of the elongated tubular body is adapted to deliver fluid into the uterus, and wherein said proximal end further comprises a one-way valve to avoid producing air bubbles in the fluid to be infused in the uterus;
    wherein said cervical seal has a conical surface and a neck at the distal end of said seal engaging the elongated tubular body to avoid any leakage of liquid at the interface of the elongated tubular body and cervical seal while providing a structure to more easily engage the cervical opening; and
    wherein said elongated tubular body has an outer diameter of about 0.059 inch to about 0.158 inch, and a length of about 10 cm to about 35 cm and said conical surface has a maximum outer diameter of about 0.500 inch to about 0.750 inch.

12. A device for expediting the non-invasive infusion of a fluid into the uterine cavity comprising:
    an elongated tubular body having proximal and distal ends;
    a slidable cervical seal located on the tubular body and slidable along the entire length of the tubular body wherein said seal engages the opening of the cervix and at least partially seals said cervical opening from the discharge of fluid contained within the uterus; and
    an opening in the distal end of said tubular body to allow the discharge of fluid;
    wherein the proximal end of the elongated tubular body is adapted to deliver fluid into the uterus, and wherein said proximal end further comprises a one-way valve to avoid producing air bubbles in the fluid to be infused in the uterus;
    wherein said cervical seal has a conical surface and a neck at the distal end of said seal engaging the elongated tubular body to avoid any leakage of liquid at the interface of the elongated tubular body and cervical seal while providing a structure to more easily engage the cervical opening; and
    wherein said neck of said cervical seal meets the conical surface of the cervical seal at an angle of from about 6° to about 27°.

13. A device for expediting the non-invasive infusion of a fluid into the uterine cavity comprising:
    an elongated tubular body having proximal and distal ends;
    a slidable cervical seal located on the tubular body and slidable along the entire length of the tubular body wherein said seal engages the opening of the cervix and at least partially seals said cervical opening from the discharge of fluid contained within the uterus; and
    an opening in the distal end of said tubular body to allow the discharge of fluid;
    wherein the proximal end of the elongated tubular body is adapted to deliver fluid into the uterus; and
    wherein said cervical seal has a conical surface and a neck at the distal end of said seal engaging the elongated tubular body to avoid any leakage of liquid at the interface of the elongated tubular body and cervical seal while providing a structure to more easily engage the cervical opening.

14. The device according to claim 13 wherein said cervical seal is comprised of an elastomeric material and further seals the interface of said cervical seal and the elongated tubular body from leaking fluid.

15. The device according to claim 14 wherein said elastomeric material is a silicon rubber of biomedical grade.

16. The device according to claim 13 wherein said distal end of said elongated tubular body includes a tip which is closed and is rounded.

17. The device according to claim 13 wherein said distal end of said elongated tubular body includes a tip which is open.

18. The device according to claim 13 wherein said fluid is an image enhancing media for conducting various diagnostic procedures in the uterus and fallopian tubes.

19. The device according to claim 13 wherein a mark is provided at about 7 cm from the distal end to assist in positioning the elongated tubular body in the uterus.

20. The device according to claim 13 wherein said elongated tubular body is comprised of a clear, flexible material.

21. The device according to claim 13 wherein said cervical seal is fixed about 7 cm from the distal end on said elongated tubular body.

22. A device for expediting the non-invasive infusion of a fluid into the uterine cavity comprising:

an elongated tubular body having proximal and distal ends;

a slidable cervical seal located on the tubular body and slidable along the entire length of the tubular body wherein said seal engages the opening of the cervix and at least partially seals said cervical opening from the discharge of fluid contained within the uterus; and an opening in the distal end of said tubular body to allow the discharge of fluid;

wherein the proximal end of the elongated tubular body is adapted to deliver fluid into the uterus; and wherein said cervical seal has a conical surface and a neck at the distal end of said seal engaging the elongated tubular body to avoid any leakage of liquid at the interface of the elongated tubular body and cervical seal while providing a structure to more easily engage the cervical opening;

wherein said elongated tubular body has an outer diameter of about 0.059 inch to about 0.158 inch, and a length of about 10 cm to about 35 cm and said conical surface has a maximum outer diameter of about 0.500 inch to about 0.750 inch.

23. A device for expediting the non-invasive infusion of a fluid into the uterine cavity comprising:

an elongated tubular body having proximal and distal ends;

a slidable cervical seal located on the tubular body and slidable along the entire length of the tubular body wherein said seal engages the opening of the cervix and at least partially seals said cervical opening from the discharge of fluid contained within the uterus; and an opening in the distal end of said tubular body to allow the discharge of fluid;

wherein the proximal end of the elongated tubular body is adapted to deliver fluid into the uterus; and wherein said cervical seal has a conical surface and a neck at the distal end of said seal engaging the elongated tubular body to avoid any leakage of liquid at the interface of the elongated tubular body and cervical seal while providing a structure to more easily engage the cervical opening;

wherein said neck of said cervical seal meets the conical surface of the cervical seal at an angle of from about 6° to about 27°.

* * * * *